(12) United States Patent
Stiros et al.

(10) Patent No.: US 7,431,901 B2
(45) Date of Patent: *Oct. 7, 2008

(54) APPARATUS AND METHOD FOR DEODORIZING CONFINED AIR SPACES WHICH UTILIZE BAKING SODA

(75) Inventors: Paul Stiros, Cincinnati, OH (US); Jeffrey Donald Painter, Loveland, OH (US); Frank Andrej Kvietok, Cincinnati, OH (US); Charles Michael Hardy, Norwood, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 167 days.

This patent is subject to a terminal disclaimer.

(21) Appl. No.: 09/775,999

(22) Filed: Feb. 2, 2001

(65) Prior Publication Data

US 2002/0106303 A1   Aug. 8, 2002

(51) Int. Cl.
  *A61L 9/00* (2006.01)
  *A62B 7/08* (2006.01)
  *B01J 3/00* (2006.01)
  *B01D 47/00* (2006.01)
  *B01D 24/00* (2006.01)
(52) U.S. Cl. ............................ 422/306; 422/1; 422/5; 422/120; 422/122; 422/123; 422/124; 422/242; 422/300; 96/153; 96/154; 96/222; 96/226; 55/528; 55/479; 261/88
(58) Field of Classification Search .............. 422/1, 422/5, 120, 122–124, 242, 300, 306; 96/153–154, 96/223, 226, 222; 55/246, 528, DIG. 5, DIG. 302, 55/479, 24, DIG. 30, 240; 261/DIG. 88
See application file for complete search history.

(56) References Cited

U.S. PATENT DOCUMENTS 5,918 A  * 11/1848  Kirkwood .................. 188/168

(Continued)

FOREIGN PATENT DOCUMENTS

FR      2.189.076         1/1974

(Continued)

*Primary Examiner*—Jill Warden
*Assistant Examiner*—Monzer R Chorbaji
(74) *Attorney, Agent, or Firm*—Brent M. Peebles; Kim W. Zerby (57) ABSTRACT

Apparatus and methods for removing malodor from the air, particularly from confined spaces are disclosed. Such devices and methods are useful for example for storing and preserving food in closed compartments such as refrigerators. The apparatus and methods utilize baking soda as the odor removing substance, either alone, or in combination with another odor removing substance, which may include activated carbon. In one embodiment, the apparatus has a detachable cartridge member which contains baking soda. In one version of this embodiment, the detachable cartridge member is used with an air moving member that draws air through the detachable cartridge member. In one embodiment, the method involves using a detachable cartridge member with an air moving member in one confined space, and using another cartridge member without the air moving member in another compartment of the confined space. In another embodiment, may also be used for emitting a scent, or other substance (including, but not limited to insecticides, air fresheners, deodorants, aromacology, aromatherapy, or any other odor that acts to condition, modify, or otherwise charge the atmosphere or to modify the environment) into the air.

14 Claims, 4 Drawing Sheets

U.S. PATENT DOCUMENTS

| | | | | |
|---|---|---|---|---|
| 1,977,760 A | * | 10/1934 | Freestone | 422/124 |
| 2,025,657 A | * | 12/1935 | Ganz | 239/55 |
| 2,784,465 A | * | 3/1957 | Strobel-Fuchs | 422/124 |
| 4,078,891 A | * | 3/1978 | Madjar | 422/116 |
| 4,294,821 A | * | 10/1981 | Neumiller | |
| 4,624,366 A | | 11/1986 | Marder et al. | |
| 4,813,344 A | * | 3/1989 | Greif | 454/156 |
| 4,844,394 A | * | 7/1989 | Randolph | 248/205.3 |
| 4,869,407 A | * | 9/1989 | Booth et al. | 222/3 |
| 4,995,556 A | * | 2/1991 | Arnold, III | 239/57 |
| 5,234,162 A | * | 8/1993 | Sullivan | 239/56 |
| 5,288,306 A | * | 2/1994 | Aibe et al. | 95/141 |
| 5,342,584 A | * | 8/1994 | Fritz et al. | 422/124 |
| 5,403,548 A | * | 4/1995 | Aibe et al. | |
| 5,603,455 A | * | 2/1997 | Lin | 239/44 |
| 5,624,311 A | * | 4/1997 | Peludat | 454/230 |
| 5,772,959 A | * | 6/1998 | Bermas | |
| D449,677 S | | 10/2001 | Denham et al. | |
| 6,495,097 B1 | * | 12/2002 | Streit et al. | 422/5 |
| 2002/0090317 A1 | | 7/2002 | Hardy et al. | |
| 2002/0178706 A1 | | 12/2002 | Kvietok et al. | |
| 2003/0010206 A1 | | 1/2003 | Painter et al. | |
| 2003/0019362 A1 | | 1/2003 | Stiros et al. | |
| 2004/0069147 A1 | | 4/2004 | Stiros et al. | |

FOREIGN PATENT DOCUMENTS

GB     2 222 775 A    *   3/1990

* cited by examiner

APPARATUS AND METHOD FOR DEODORIZING CONFINED AIR SPACES WHICH UTILIZE BAKING SODA

This application is a continuation of PCT applications US/0013531, filed on May 18, 2000, which is a continuation of PCT application US/00/03010, filed on Feb. 4, 2000.

FIELD OF THE INVENTION

The present invention relates an apparatus and method for removing malodor from the air. Such devices and methods are useful for example for storing and preserving food in closed compartments such as refrigerators.

BACKGROUND OF THE INVENTION

Nowadays, refrigerators have become a common appliance in virtually every household and typically are used for storage and preservation of food, in particular of fresh food such as fruits, vegetables, dairy products, and the like. It is desirable to keep the food items fresh as long as possible in the refrigerator.

It is a well known problem that many food items tend to release malodors into the air which are then captured in the limited air space in a refrigerator. Not only are these malodors unpleasant and offensive to the user of the refrigerator, they can also have a negative impact on the quality of other foods in the refrigerator. For example, it is known that some foods emit strong odors (e.g. fish, boiled eggs, onions, etc.) and that these odors can transfer to other nearby foods and hurt the taste and freshness of those foods. A common example is transfer of odors into an open container of orange juice or of milk resulting in a noticeable degradation in their taste. It is also well known that malodors from some vegetables (onions, garlic) can transfer to other foods stored within a vegetable drawer. This problem is aggravated when the vegetable drawer is sealed such that there is very little air exchange with the larger compartment of the refrigerator (herein referred to as the "fresh food compartment") and when vegetables have been cut or are stored without any outer wrapping. This problem of odor transfer is particularly acute in the case of ice cubes where odors from the fresh food compartment of the refrigerator can be transferred to the ice in the freezer compartment of the refrigerator. This is especially true in the case of refrigerators in which there is air exchange between the fresh food and freezer compartments, and especially in the case of refrigerators with built-in ice-makers.

A common attempt to solve this odor contamination problem is the use of an opened box of baking soda, especially in the refrigerators. However, this static method is not very effective, because the bulk of the baking soda is not exposed to the contaminated air, and the air movement around the baking soda is minimal. In addition, there is the possibility that an opened box of baking soda could be tipped over, creating a mess in the refrigerator.

The ARM & HAMMER® Division of the Church & Dwight Co., Inc. of Princeton, N.J., U.S.A. has also recently introduced a product known as FRIDGE-n-FREEZER™ FLOW-THRU FRESHENER™ that attempts to address some of these problems. The FRIDGE-n-FREEZER™ FLOW-THRU FRESHENER™, as shown in U.S. Pat. No. 4,624,366, is essentially a box of baking soda that has openings on the sides to increase the amount of surface area of the box through which the baking soda is exposed. The baking soda is contained in the box by a "cloth filter" nonwoven material that is positioned between the baking soda and the openings in the box. This product, however, suffers from the disadvantages that the baking soda is still packed so densely in the box that air is unable to flow through the baking soda, or be drawn through the baking soda, and this product must rely on air convection and diffusion to bring malodors adjacent to the openings on the box.

There also exist in the art devices for deodorizing confined spaces such as disclosed for example in U.S. Pat. No. 5,403,548 and in U.S. Pat. No. 5,772,959. However, these devices as such fail to be capable of deodorizing those complexly structured confined spaces which comprise portions which are not reached by normal air convection. In these portions which include, for example, drawers for fresh fruits and vegetables in a refrigerator, malodors may be trapped and hence may not be reached by deodorizing devices placed in the main compartment.

It is therefore an object of the present invention to provide an apparatus and a method for deodorizing confined spaces which overcomes the disadvantages of the prior art.

SUMMARY OF THE INVENTION

The present invention relates to an apparatus and a method for removing malodor from the air, particularly within confined air spaces. The apparatus may utilize baking soda alone, or with another odor removing substance, which may include, but is not limited to, activated carbon.

In one non-limiting aspect, the present invention provides an air deodorizing device comprising a detachable cartridge member. The air deodorizing device has an air flow path from an air inlet to an air outlet. The cartridge member comprises a filter member and is arranged with the filter element in interaction with the air flowing along the air flow path. The air deodorizing device further comprises an air moving member for moving air along the air flow path.

In another non-limiting aspect, the present invention provides an apparatus for deodorizing air in confined spaces comprising a first filter member, a second filter member, and an air moving member wherein both the first filter member and the second filter member are attachable to the air moving member.

In another non-limiting aspect, the present invention provides a method for deodorizing air in confined spaces comprising the steps of:
(a) providing a first filter member;
(b) providing a second filter member;
(c) positioning the first filter member inside the confined space;
(d) positioning the second filter member inside the confined space independent from the position of the first filter member; and
(e) removing malodor molecules from the air of the confined space using the first filter member and the second filter member.

DETAILED DESCRIPTION OF THE INVENTION

The apparatus and method for deodorizing air in confined spaces of the present invention is suitable for use in various confined spaces, including, but not limited to, refrigerators, closets, clothes dressers, and the like.

The apparatus of the present invention can be provided in any suitable configuration. An apparatus useful in the present invention may comprise a passive filter member, a forced air filter member, or combinations of one or more passive filter members and one or more forced air filter members. The apparatus of the present invention preferably comprises at least one passive filter member which can be used with an air moving member and which can be detachable from an air moving member and used separately. This greatly enhances the flexibility of the use of the apparatus of the present invention. The filter members of the apparatus of the present invention can have any size and shape as long as they can be used with the air moving member and can also be of the same shape and/or of the same size.

The term "passive filter member" as used herein refers to those filter members which only rely on air convection and on diffusion to bring malodors within reach of the filter media in the member. The term "forced air filter member" as used herein refers to those filter members which are associated with a forced air moving member which draws air into the device past or through a filter member containing a filter media and increases air flow past or through the filter media above that which is achieved through normal air convection in the confined space. As used within this disclosure, a forced air filter member consists of a filter member and an air moving member. A filter member suitable for the forced air filter member may be a passive filter member according to the above definition.

Figure 1:
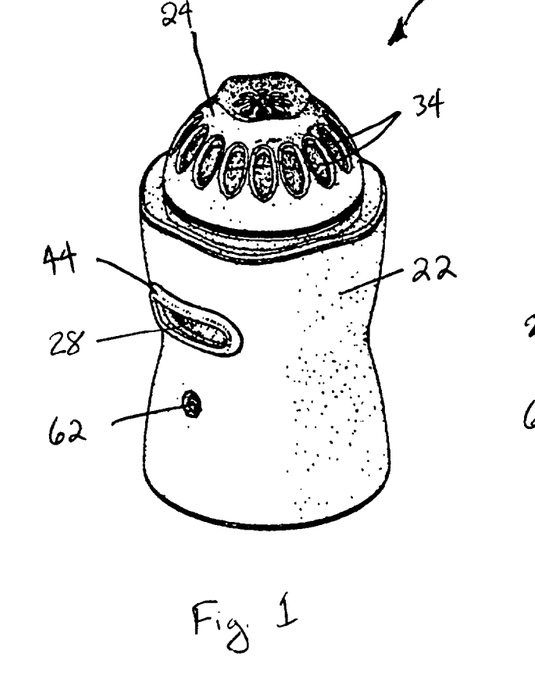
FIG. 1 is a perspective view of one embodiment of the apparatus of the present invention with a cartridge member in place thereon.

One non-limiting embodiment of the apparatus or air deodorizing device (or simply "the device") of the present invention is shown in FIG. 1. The apparatus 20 comprises an air moving member 22 and one or more passive filter members, such as filter member 24. The filter member 24 is associated with the air moving member 22. That is, the filter member 24 is used together with the air moving member 22. The filter member 24 is preferably in contact with the air moving member 22, and may be temporarily attached thereto, or held in contact therewith. In the embodiment shown, the air moving member 22 serves as a base for the filter member 24. The air moving member 22 has an air flow path from one or more air inlets 26 to one or more air outlets 28. (There may, for example, be another air outlet 28 on the opposite side of the air moving member from the air outlet 28 shown in FIGS. 1 and 2.) The filter member in this embodiment comprises a cartridge member (or simply "cartridge") 24 and is arranged with the filter element in interaction with the air flowing along the air flow path. In this embodiment, the cartridge member 24 housing the filter element is detachable from the air moving member 22.

The term "detachable" as used herein refers to members which can be easily removed, in particular where no tools such as screw drivers are needed. Preferably, no excessive forces are needed for detaching the cartridge member 24. In addition, the cartridge member 24 is preferably directly accessible from outside the air moving member (or other device) 22, and the cartridge member 24 can be removed without opening doors or the like, by holding the air moving member 22 of the present invention in one hand and by removing the cartridge member 24 with the other hand, or by simply lifting the cartridge member 24 off the air moving member 22.

Figure 3:
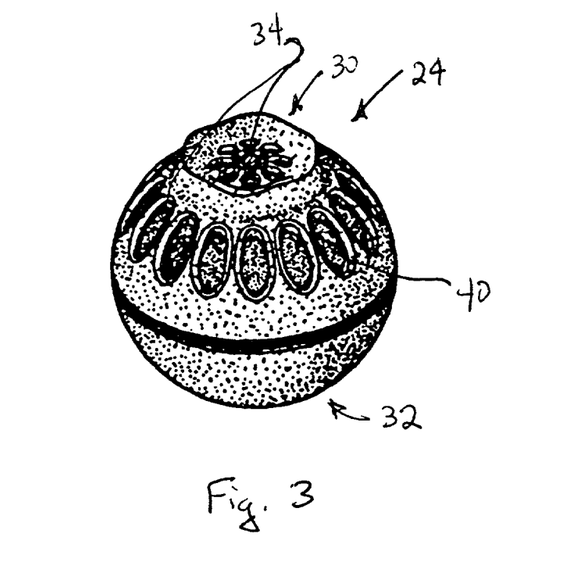
FIG. 3 is a perspective view of the cartridge member used in the embodiment shown in FIG. 1.
Figures 3, 4:
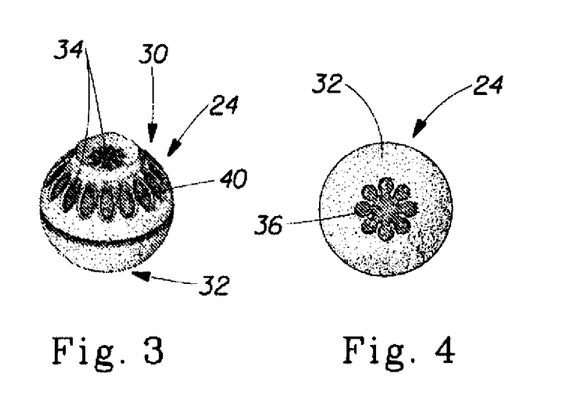
FIG. 4 is a bottom view of the cartridge member.
Figure 4:
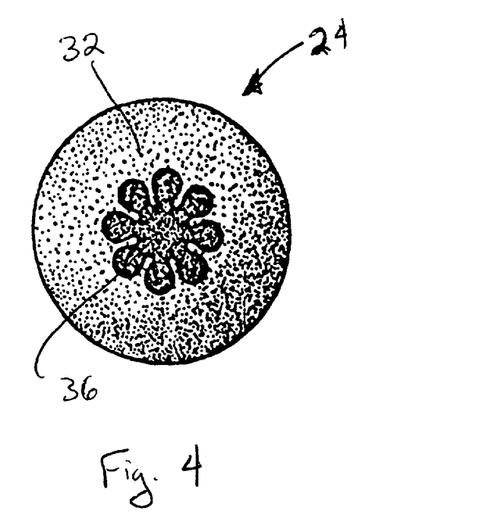

As shown in FIGS. 3 and 4, the cartridge member 24 has a top portion 30 and a bottom portion 32. The cartridge member (i.e., the filter member) 24 may also comprise one or more air inlets 34, one or more air outlets 36, and an air flow path through the filter member from the air inlets to the air outlets. The filter member 24 in this embodiment sits on the top portion of the air moving member so that the outlets 36 on the bottom portion 32 of the filter member 24 is at least partially in alignment with the air inlets 26 on the air moving device 22. In this embodiment, a filter element (or "filter") 40 is disposed in the filter member 24 so that it comes into contact with the air flowing along the air flow path. The filter element 40 may be arranged as a flow by filter or as a flow through filter. If the filter element 40 is arranged as a flow through filter, the filter element, and the filter medium are preferably sufficiently pervious to air so that air can be conveyed through the filter member. The filter member 24 may comprise a support for the filter medium, for example, in the form of a foam, a nonwoven material or a woven material.

The deodorization of the air in the air deodorizing device of the present invention is enhanced by increasing the air flow through the filter member by means of an air moving member. To improve the malodor removal performance and to simplify the mechanical construction of the air deodorizing device of the present invention, the filter member and the air moving member are preferably arranged such that substantially all air drawn in by the air moving member is forced to flow through the filter member before it penetrates the air inlet of the air moving member. In other words, the air inlet of the cartridge member is preferably in communication with the air inlet of the air moving member. In this setup, only one air path connection is needed between the filter member and the air moving member and hence complexity is decreased. Furthermore, withdrawal of the cartridge member is greatly simplified if only one connection has to be disengaged. Any disengageable air flow connection may of course comprise sealing members to improve air flow performance. Any such connection may further comprise a mechanical engaging members to stabilize the connection.

The component portions of the embodiment of the apparatus 20 shown in FIG. 1 will now be examined in greater detail.

Figure 2:
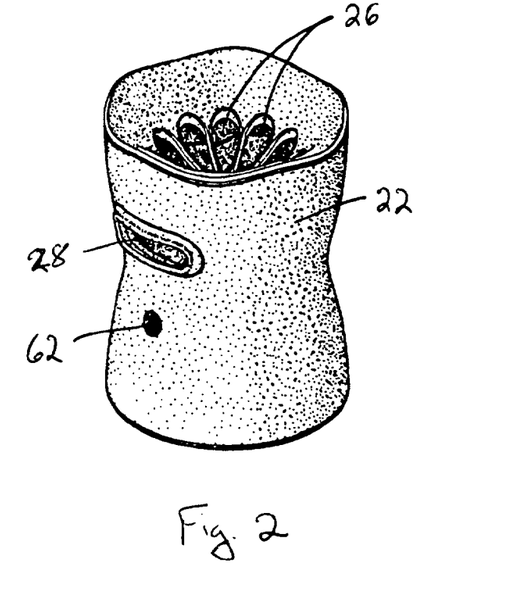
FIG. 2 is a perspective view of the apparatus shown in FIG. 1 with the cartridge removed.
Figure 5:
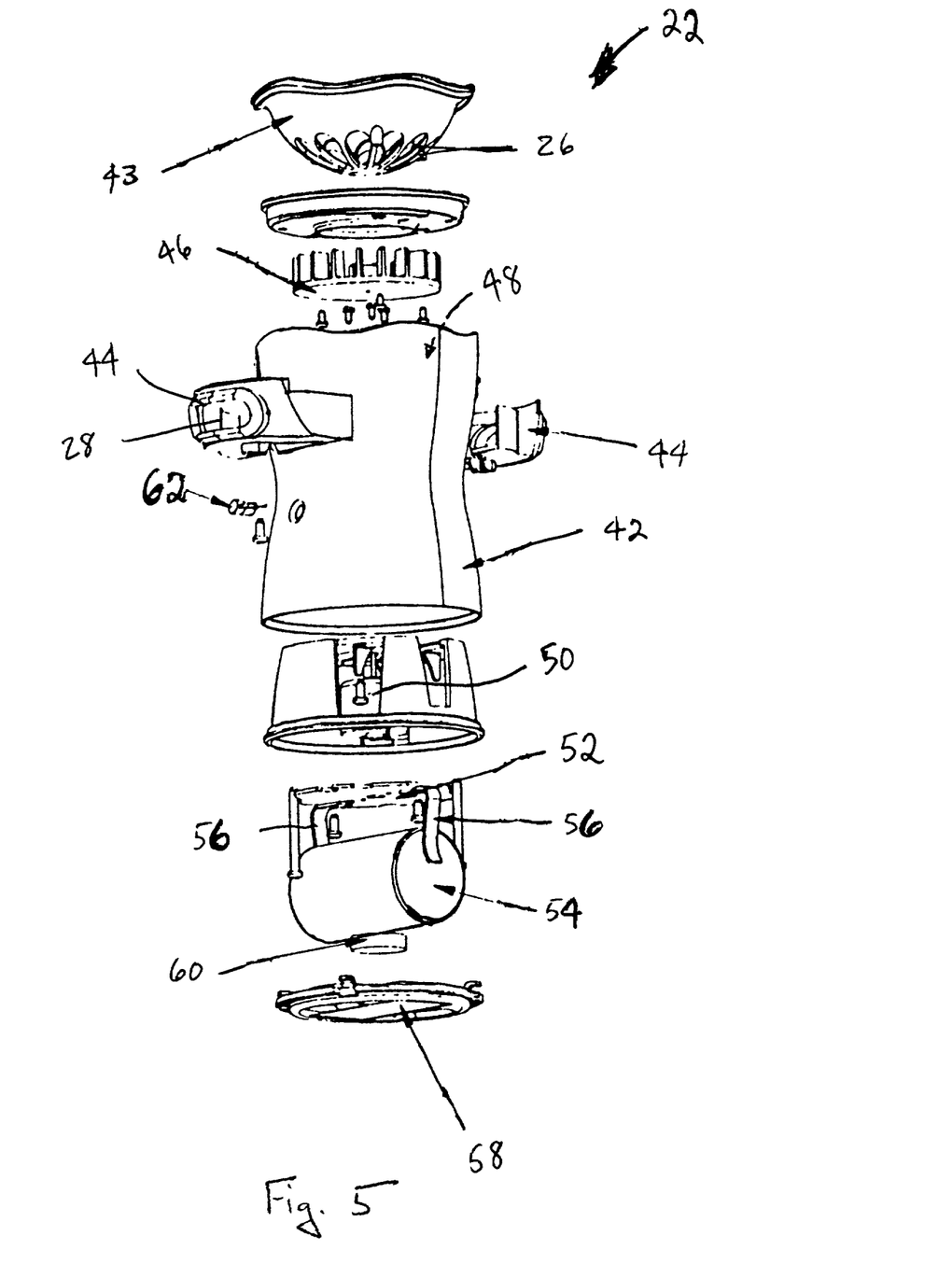
FIG. 5 is an exploded perspective view of the embodiment of the apparatus shown in FIGS. 1 and 2.

FIG. 5 is an exploded view of the air moving member shown 22 in FIGS. 1 and 2. The air moving member 22 comprises a main housing 42 into which two air outlet fixtures 44 are installed. The main housing 42 is sized to contain all of the elements described below. An air inlet member 43 is joined to the main housing 42 to form the top of the air moving member 22. In this embodiment, the filter member 24 will be placed on top of the air inlet member 43 so that air is drawn through the filter member 24 via a suction force. The air can be drawn by a wide variety of suitable air moving members such as, for example, fans and blowers. One suitable air moving member to deliver this suction force is a centrifugal fan 46. The centrifugal fan 46 is contained in a small chamber 48 which helps to maximize the air flow, allowing air to be drawn in near the center of the impeller and expelled perpendicular to the entry direction and through the air outlets 28 of the air moving member 22. The air outlet fixtures 44 are preferably positioned in the main housing 42 such that the rotation of the fan 46 is visible through these outlets. This allows a means of confirming that the fan 46 is operating. Preferably, the air moving member moves at least about 100 mL of air per second through the air inlet into the device, more preferably at least about 200 mL/s most preferably at least about 300 mL/s. A suitable member for driving the fan is a small motor, for example a DC motor available from Mabuchi Motor Co., LTD., Japan, under the designation of RF-330TK.

The motor is controlled by a circuit board 52. The air moving members of the present invention are preferably powered electrically. Many electrical power sources could be used, including domestic AC electrical power or power from a static power supply. Alternatively, and preferably, electrical power may be supplied by means of a battery, preferably a dry alkaline cell battery, or a rechargeable battery. In this example, power for the motor is supplied by means of a battery 54, preferably a 1.5 V dry alkaline cell battery, or a rechargeable battery, which is connected to the circuit board by two battery contacts 56. The battery is held into the device by a battery door 58 onto which is adhered a small piece of foam 60 which helps to maintain a tight fit of the battery into the device. The circuit board also contains circuitry controlling a light emitting diode (LED) 62 which is described in greater detail below.

In this example of the device of the present invention, the battery, fan, motor, and circuitry are designed to require very low power draw, enabling the device 20 to run continuously for a long period of time. Preferably, this embodiment of the device 20 continuously draws less than 20 mA, more preferably less than 10 mA, and most preferably less than 8 mA. To require infrequent battery replacement, the replaceable power supply of this embodiment preferably is designed to last at least one month, more preferably at least two months, yet more preferably at least three months, most preferably at least four months.

To facilitate ease of use to the user of the device, an indicator is preferred to announce the approaching need to replace the battery. An indicator could be audible, such as a buzzer or whistle; or visual such as a blinking light or raised flag for example. In this example, the indicator is a blinking light emitting diode (LED) 62 which blinks a few dozen times per minute when the voltage of the replaceable power unit falls below about 0.9 V. The LED of this example operates at 3.0 V, much higher than the voltage supplied by the replaceable battery. To enable the operation of this LED, a permanent 3.0 V lithium cell is mounted to the circuit board to power this circuit. The lithium cell is expected to last the lifetime of the device, approximately five years.

FIG. 3 is a perspective view showing one non-limiting example of a filter member 24. This example of a filter member 24 is in the form of a cartridge. The cartridge enables the filter medium to be conveniently handled without the filter medium from spilling out and/or coming into contact with articles in the spaces within which the filter member is placed. The filter member of the present invention comprises an air inlet 34, an air outlet 36, and air flow path through the filter member 24 from the air inlet to the air outlet.

The filter member 24 contains a filter element or filter 40. The filter element 40 can be in any suitable configuration, including, but not limited to, disc-shaped, oval, parallelepiped-shaped, rectangular, cube-shaped, cuboid-shaped, cylindrical-shaped, pyramid-shaped, spherical-shaped, irregularly-shaped, or other configuration. In the embodiment shown in the drawings, the filter element 40 is in the general shape of a sphere, a cylinder, or in the shape of several disks of various diameters and thicknesses such that when the disks are placed atop one another they approach the shape of a sphere or a portion thereof.

The filter medium is disposed in the filter member 24 of the present invention such that it comes into contact with the air flowing along the air flow path. The filter element 40 may comprise a support for the filter medium, for example, in the form of a honeycomb, a foam, a nonwoven web or a woven web, or an open-pore reticulate structure, such as a foam or a mesh.

Deodorization of the air to remove malodors in the device of the present invention may be achieved by a filter medium that neutralizes the odors, that absorbs the malodor molecules, and/or that adsorbs the molecules constituting a malodor onto a surface of a filter medium. The term "adsorption" is well defined in the art and refers to the adherence of molecules to surfaces which effectively reduces the mobility of these molecules to the two dimensions of the surface. Those molecules remaining in the air will then diffuse so that further molecules come into contact with the surface and subsequently will be adsorbed. Consequently, most of the malodor molecules will travel into the proximity of one of the surfaces at some point in time so that finally most of the malodor will be removed from the air.

A filter medium suitable to be used in the filter member(s) of the present invention may comprise sodium bicarbonate (i.e., baking soda) alone, or baking soda with another odor removing substance. Other odor removing substances may include, but are not limited to activated carbon, cyclodextrin, zeolites, alumina, silicates, carbonates, ozone, acid-treated media, base-treated media, metals (such as silver and platinum), doped media, any other known odor removing substance, and combinations thereof. Activated carbon is known to be a very effective filter medium for adsorption of odors due to its high specific surface area. The filter member 24 of the present invention may further comprise agents supported on the filter element 40 to specifically attack certain malodors such as those comprising S atoms or N atoms. Additionally, or alternatively, the filter member of the present invention may comprise a filter medium capable of removing ethylene from the air, such as a filter medium comprising potassium permanganate.

If activated carbon is used, the filter member(s) of the present invention preferably comprise at least about 2 grams, more preferably at least about 5 grams, and most preferably at least about 10 grams of activated carbon. Preferably, the filter members of the present invention comprise less than about 100 grams, more preferably less than about 50 grams, yet more preferably less than about 40 grams, and most preferably less than about 30 grams of activated carbon. A wide variety of activated carbon based filter media is known in the art. Suitable forms of supported activated carbon are the reticulated polyurethane foam products which are commercially available from Helsa-Werke, Helmut Sandler GmbH & Co. KG, Germany, under the designations Helsa-tech 8126, 8139, 5600, and 5615.

The filter medium can be arranged in any suitable manner to form the filter element 40. Several non-limiting examples are as follows. The filter medium may be provided in a loose form (such as granules, pellets, or other form) within the filter member 24. Preferably, if the filter medium is provided in loose form, there is (but need not be) some type of containment component that prevents the filter medium from leaking or falling out of the filter member 24. The filter medium can be provided either on a supporting component, in a supporting component, or both on and in a supporting component. In one non-limiting example, the supporting component could be a pervious material, such as a pervious piece of foam. The filter medium could be provided in the form of particles, or some other form, that is disposed on or within the piece of foam, or other pervious material. Alternatively, or additionally, the filter medium could be integrally formed with such a supporting material. One non-limiting example of this would be for baking soda to be included in the composition that is used to form a pervious foam material. The filter medium can be provided in one or more containers that comprise the filter element 40. These container(s) can comprise boxes, bags (such as tea bag-type elements), sachets, or other containers. These containers may be made of a porous material, or may have holes or apertures therein to facilitate air flow. The filter media may be provided in and/or on flat or corrugated or textured filter elements (which may resemble, but are not required to resemble, furnace filters (permanent or disposable)). These containers or filter elements, if there is more than one of each, can be arranged in any suitable relationship to each other, including, but not limited to stacked, side-by-side, with or without space therebetween. The examples of types of filter elements described above can also be combined in any manner to produce yet other filter elements.

Figure 6:
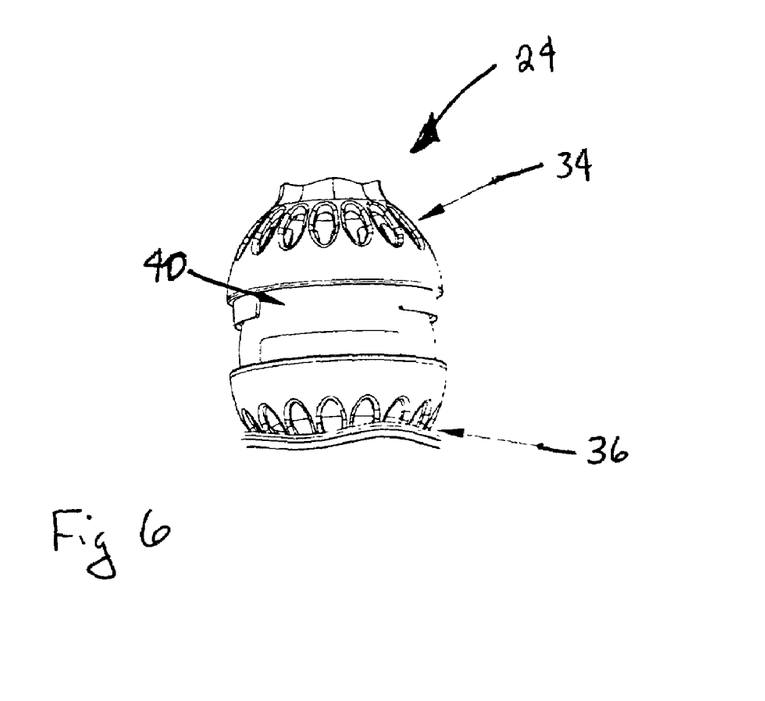
FIG. 6 is a side view of the cartridge shown in the preceding figures which is partially opened to show the filter medium.
Figure 7:
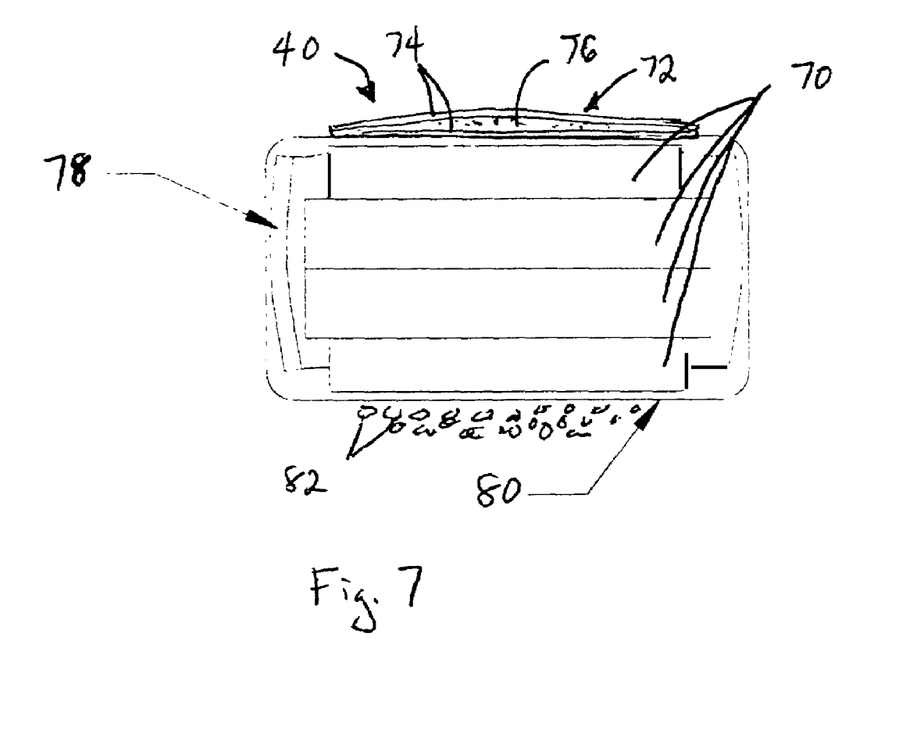
FIG. 7 is a schematic cross-section of the filter medium shown in FIG. 6.

FIG. 7 is a schematic cross-section of one non-limiting example of a filter element (or "filter") 40 suitable for use in the embodiment of the filter member 24 shown in FIGS. 3, 4, and 6. The filter element 40 shown in FIG. 7 combines several of the types of filter elements described above. (It should be understood, however, that this is primarily for the purposes of illustration of the various different types of filter elements, and it is not necessary that a filter element comprise all of these components.)

The filter element 40 shown in FIG. 7 comprises several disks 70 which can have the filter media (such as baking soda, activated carbon, or both) thereon and/or therein. The disks 70 can be made of any material suitable for this purpose. If it is desired to allow air to flow through the filter element 40, the disks should be pervious to air flow. In the embodiment shown, the disks 70 are comprised of a porous foam that is pervious to air flow. The disks 70 are placed atop one another. Additional filter media, such as baking soda, activated carbon, or both, can be placed on top of the stack of disks 70, below the stack of disks, or on the sides of the stack of disks (e.g., wrapped around the stack of disks). These filter media can be arranged in a virtually unlimited number of combinations of different manners (e.g., different spatial relationships and different types of filter media).

For example, in one non-limiting embodiment, a container, such as a sachet or small pervious bag of baking soda 72 can be placed on top of the disks 70. The sachet 72 shown in FIG. 7 comprises a pair of porous side walls 74 having baking soda 76 therebetween. The baking soda 76 can be in any suitable form, including, but not limited to powder or granules. The container 72 can have the baking soda disposed therein in sufficient thickness that air is unable to flow through the container 72 as a result of action of the fan, and the baking soda 76 can only serve to deodorize air that moves past the container 72. Preferably, however, the container of baking soda 72 has the baking soda disposed therein (whether it be by distributing the baking soda in a sufficiently thin layer, by placing portions of the baking soda into separate compartments, or by some other mechanism) such that air pulled in by the fan will flow through the container of baking soda 72 without an excessive drop in pressure (or air flow rate).

The disks 70 can have baking soda and/or activated carbon affixed thereto. Around the stack of disks 70 is wrapped a first wrapping (or if there is no other wrapping, "the wrapping"), such as a piece of nonwoven material 78. The first wrapping 78 can have any suitable filter media thereon. In one non-limiting example, the first wrapping 78 can have baking soda on the inside portion thereof. In another non-limiting example, the first wrapping 78 can support potassium permanganate for ethylene removal. To prevent spillage of any filter media particles, this entire assembly may be contained in a second wrapping, such as a piece of woven nylon 80. In one embodiment, the nylon is stretched to a point such that the average pore size of the nylon is less than about 0.5 mm$^2$. In another non-limiting example, a larger sachet with baking soda therein could be wrapped around the stack of disks 70. This larger sachet can be used as a replacement for the first and/or second wrappings, or in addition to the first and/or second wrappings.

Additional filter media can also be located below this assembly. For example, in one non-limiting embodiment, media such as baking soda granules 82, or another sachet can be provided underneath the filter to provide additional odor removal capacity. In other non-limiting embodiments, instead of comprising a stack of disks, the filter element could comprise arrangements of one or more containers (including, but not limited to a stack or row of containers, with or without space therebetween) containing baking soda. Numerous other embodiments are possible. It should also be understood that the filter element 40 of the present invention need not comprise all the elements described herein (which are shown merely to illustrate some of the possible variations), but may instead comprise only one, or more, of these elements.

Confined spaces often have complex structures so that normal air convection does not reach every corner of the confined space. Such complex structures for example include separate compartments such as drawers or hollow elements inside the confined space. Therefore, it is insufficient to deodorize such confined spaces with only a single device, even a forced air device having a fan.

In accordance with one aspect of the method of the present invention, it is possible to also deodorize those portions of the confined space which are not sufficiently accessible to normal air convection. This is achieved by utilizing more than one filter member whereby each of those filter members can be positioned independent of each other whereby one of the filter members optionally may be used while connected to an air moving member.

A confined space for which one aspect of the method of the present invention is particularly suitable comprises a compartment which is within the confined space but which is separated from the remainder of the confined space. In this case, one of the filter members may be placed in the separate compartment and another filter element may be placed in the remainder of the confined space. With the method of the present invention it is therefore possible to deodorize all compartments in a confined space such as a refrigerator (which has enclosed compartments for vegetables, meats, etc.), a closet (which has shoe storage closets, clothes storage containers, etc.), or the like. In particular when the separate compartments differ in size, it may be beneficial to place a forced air filter member in the larger compartment and a passive filter member in the smaller compartment.

A forced air device will enable removal of more malodors to happen more quickly than a passive device by increasing the rate of air contact with the adsorbing media. As such, a forced air device as described above is suitable for use in the large area of a confined space (e.g. the fresh food compartment of a refrigerator, a closet, etc.) as it has the ability to move the relatively large volume of air in these spaces, typically 50 to 800 liters, through or past the filter media. A passive device is suitable for use in the smaller compartments within a confined space (vegetable drawers, shoe storage containers, etc.) where diffusion alone is effective at moving air to the filter media, and where the air is not accessible to the forced air device.

The apparatus of the present invention is used by inserting a battery in the air moving member 22 (if one is not already therein), and placing the air moving member 22 along with a cartridge member 24 in a confined space to be deodorized. The cartridge member 24 may be placed directly on top of the air moving device 22, and will remain held in place thereon by gravitational forces and the surface topology of the interfacing parts of the cartridge member and the air moving member. For instance, as shown in the drawings, the interfacing parts of the cartridge member 24 and the air moving member 22 may match each other such as if each has a complementary hemispherical design. The forced air filter apparatus 20 is preferably placed in one of the larger confined spaces to be deodorized, such as in the interior of a refrigerator.

A second (and third, fourth, etc.) cartridge member 24 may be placed in one of the smaller confined spaces to be deodorized, such as in one or more of the drawers of the refrigerator, and used as a passive filter. Alternatively, one or more of the cartridge members 24 could be placed in one of the larger confined spaces to be deodorized and used as a passive filter, and the entire apparatus could be placed in the larger confined space to be deodorized. In addition, the cartridge members can be placed in other confined spaces to be deodorized, which other spaces are independent of the location in which the apparatus is placed. For example, the apparatus could be placed in a refrigerator, and the additional cartridge members could be placed in dresser drawers, or any other confined spaces.

When the cartridge member 24 on the air moving member 22 is exhausted, the cartridge member 24 can simply be lifted off the air moving member 22, and replaced with a fresh cartridge 24. The cartridge members 24 in the other confined spaces can similarly be replaced with fresh cartridges when they are exhausted.

The present invention can provide several benefits, especially in confined spaces such as refrigerators, including, but not limited to: removing malodor from said confined spaces; removing ethylene from said confined spaces; maintaining the fresh odor of said confined spaces; reducing the transfer of airborne bacteria in said confined spaces; maintaining the freshness of food items; improving the quality of food items; maintaining the fresh taste of food items; preventing the transfer of odors between two food items; extending the useful life of food items; keeping food items fresh over a longer period of time; reducing spoilage of food items; reducing the incidence of freezer burn of food items in a freezer compartment; maintaining the fresh taste and/or odor of ice cubes (preferably ice cubes made by an automatic ice maker); increasing the cooling efficiency of a refrigerator; preventing or reducing the formation of ice crystals on ice cream in an opened or partially-sealed box stored in a freezer compartment; and combinations thereof. The present invention further relates to the use of said apparatus to achieve said benefits (i.e. technical effects).

The apparatus can be provided in the form of a package or kit which comprises: (a) an apparatus selected from the group consisting of a passive filter member, a forced air filter member, and combinations thereof; (b) optionally, a package containing said apparatus; and (c) optionally informational indicia, including printed matter such as a set of instructions, in association with said apparatus or the package to communicate said benefits to a consumer.

The apparatus is optionally, but preferably contained in a package that protects the apparatus during shipment and/or makes the apparatus easier to display in a retail store or more appealing to consumers. The optional package can be any number of suitable packages, including but not limited to: cardboard boxes, bubble-wrap films, thermo-form plastic packaging, expanded cellular polystyrene (e.g. STYROFOAM™), and the like.

The apparatus may also be provided with optional informational indicia which communicates the benefits (i.e. technical effects) of the apparatus to consumers. Without the informational indicia, consumers who otherwise might not use the apparatus (e.g. because they were not aware of the potential benefits/technical effects derived from using the apparatus), will use the apparatus to obtain the benefits, such as preserving the quality of food, and the like.

Informational indicia can be provided in association with the apparatus itself or, when the present article comprises a package, in association with the package. As used in this context, the phrase "in association with" means the informational indicia (e.g., a set of instructions) are either directly printed on the apparatus itself (or package itself) or presented in a different manner including, but not limited to, a video tape, a brochure, print advertisement, electronic advertisement, and/or verbal communication, so as to communicate the set of instructions to a consumer of the article of manufacture. Informational indicia can include, but is not limited to: a set of instructions that direct a consumer how the steps need to be carried out (such as the methods of use described herein) to obtain the communicated benefits; diagrams, pictures, and/or logos which communicate the benefits and steps which need to be carried out to obtain the benefits; and the like.

Numerous other embodiments of the apparatus and method of the present invention are possible. A couple of non-limiting examples are described below.

Figure 8:
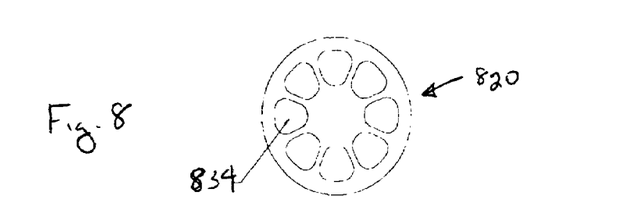
FIG. 8 is a top view of an alternative embodiment of the device of the present invention.
Figure 9:
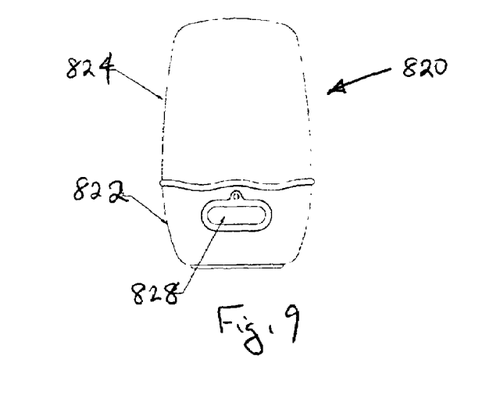
FIG. 9 is a side view of the device shown in FIG. 8.

FIGS. 8 and 9 show an alternative embodiment of the device of the present invention. In FIGS. 8 and 9, a device 820 is provided which comprises at least one air inlet 834, air outlets 828 on each side of the base 822 and a removable and replaceable filter member 824. The filter member 824 is placed onto the base 822 such that air flow from a fan draws air through the top of the filter member 824 and through the air outlets 828 on the base 822.

In this example, the filter member 824 contains a filter element and a battery. The filter element is designed to exhibit the same useful lifetime as that of battery so that both may be replaced as a single unit. The filter member 824 contains two metal contacts allowing an electrical current to flow from the battery to the base 822. The filter element of the device can be the same system as described in the embodiment shown in FIG. 1. The filter element can be shaped such that a battery, such as a 1.5 volt dry alkaline "D" battery, fits inside a void in the filter element.

Similar to the embodiment shown in FIG. 1, the base 822 contains a fan, motor and a circuit board which controls the motor and an LED (not shown) which blinks to indicate the upcoming need to replace the filter member 824 containing the battery and filter medium. Further, the base 822 also contains metal contacts allowing current to flow from the battery (contained in the filter assembly) to the motor.

Figure 10:
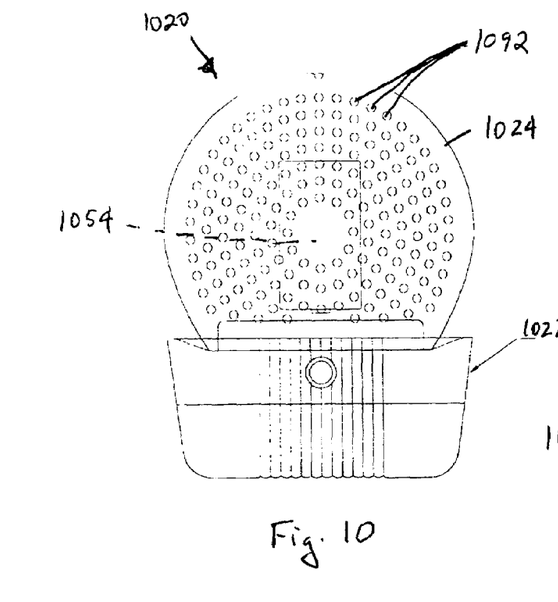
FIG. 10 is a side view of another alternative embodiment of the device of the present invention.
Figure 11:
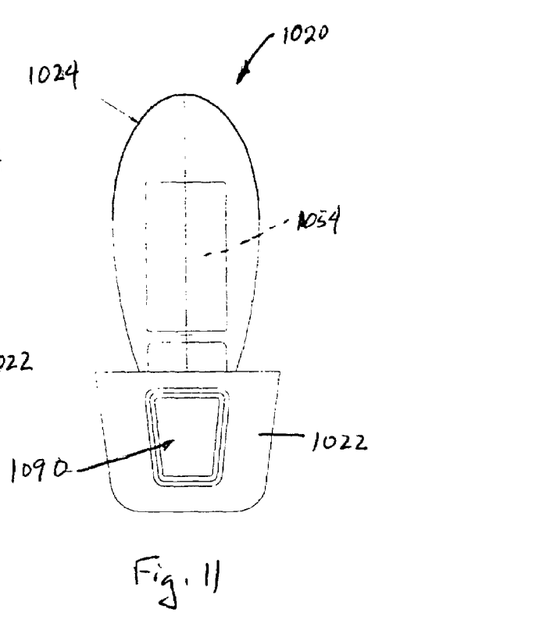
FIG. 11 is an end view of the device shown in FIG. 10.

FIGS. 10 and 11 show another alternative embodiment of the device of the present invention. In FIGS. 10 and 11, a device 1020 is provided which comprises an air inlet 1090 on each side of the base 1022, multiple air outlets 1092, and a removable and replaceable filter element member 1024. The filter member 1024 is placed onto the base 1022 such that air flow from a fan draws air through the air inlets 1090 in the base 1022, through the filter medium inside the filter member 1024, and out through the air outlets 1092 in the filter member 1024.

In this example, the filter member contains a filter element and a battery. The filter element is designed to exhibit the same useful lifetime as that of battery so that both may be replaced as a single unit. The filter member contains two metal contacts (not shown) allowing an electrical current to flow from the battery 1054 to the base. The filter element of the device can utilize the same system as described in the example of FIG. 1. The filter element is shaped such that air is forced from the base into the bottom and middle of the filter element and then must travel outward through the filter element to flow through the air outlets 1092. Further, this filter element is shaped such that a 1.5 volt dry alkaline "D" battery fits inside a void in the filter element.

In this example, the base 1022 may contain multiple fans and motors to provide more air flow through the filter assembly. Because of the filter housing geometry, the best performance with this device is obtained by using two centrifugal fans, powered by one or two motors. The base contains a circuit board which controls the motors and an LED (not shown) which blinks to indicate the need to replace the filter member containing the batter and filter medium. Further, the base 1022 may also contain metal contacts allowing current to flow from the battery 1054 (contained in the filter assembly) to the motors. Optionally, the base 1022 may be designed to contain the replaceable battery, eliminating the battery from the filter unit.

The present invention may also be used for emitting a scent, or other substance (including, but not limited to insecticides, air fresheners, deodorants, aromacology, aromatherapy, or any other odor that acts to condition, modify, or otherwise charge the atmosphere or to modify the environment) into the air. For example, it is possible to use the device for emitting a scent into the air either with or without including the technology described herein to remove malodors from the air. To illustrate this, it is possible to replace the filter element with scent-containing media, or alternatively to add scent-containing media to any of the filter elements described herein. Scent-containing media can include, but is not limited to scented gels, scented beads, scented cellulose, scented activated carbon, or other scent-containing media.

Such a use of the present invention may, but need not include baking soda. The device described herein can be used for emitting a scent or substance in any of the manners specified herein for use in removing malodors from the air. For example, a first emitting member could be used for emitting a substance with the air moving member, and a second emitting member could be used independently of the first emitting member and air moving member to passively emit the same or different substance into the air. The device can be provided to consumers in the form of a kit which contains air deodorizing media, substance emitting media, or both. Consumers can also use these various types of cartridges interchangeably with the air moving member or separately from the air moving member.

When the device is used for emitting substances, it will operate in the same manner as described above when it is used for deodorizing confined spaces. Thus, for example, a cartridge 24 with emitting media contained therein can be placed on top of the air moving member 22, and air will be drawn into the cartridge past or through the emitting media, and will be emitted through the air outlets 28 of the air moving member. When the device is used for emitting substances, it is possible to effectively use the device for emitting substances in even larger confined spaces, such as in a room, or a closet.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A system for deodorizing air, comprising:
a passive filter member comprising a first filter element, the first filter element comprising a first filter medium which at least partially comprises sodium bicarbonate, and the passive filter member being adapted to remove malodor from air without the assistance of an air moving member; and
a forced air filter member having an air flow path from an air inlet to an air outlet, the forced air filter member comprising a second filter element and an air moving member, the second filter element comprising a second filter medium which at least partially comprises sodium bicarbonate, the air moving member having a housing and being adapted to move air along the air flow path and through at least a portion of the second filter medium, the second filter element being positioned on an upper exterior portion of the housing and detachable from the air moving member, interfacing parts of the second filter element and the upper exterior portion of the housing having complimentary surface topography;
and the passive filter member being interchangeable with the second filter element for positioning on the exterior portion of the housing.

2. The system for deodorizing air of claim 1, the passive filter member being of the same shape as the second filter element.

3. The system for deodorizing air of claim 2, the passive filter member being the same size as the second filter element.

4. The system for deodorizing air of claim 1, each of the passive filter member and the second filter element comprising a cartridge.

5. The system for deodorizing air of claim 4, each cartridge comprising a top portion and a bottom portion and being provided with one or more air inlets in the top portion and one or more air outlets in the bottom portion.

6. The system for deodorizing air of claim 5, the upper exterior portion of the air moving member comprising a housing having an air inlet therein, and the second filter element cartridge being positioned on the upper exterior portion of the housing of the air moving member so that the one or more air outlets on the bottom portion of the second filter element cartridge are at least partially in alignment with the air inlet of the air moving member.

7. The system for deodorizing air of claim 1, the air moving member comprises a fan and the sodium bicarbonate in each of the first filter member and the second filter member being sufficiently pervious to air so that the fan can convey air through the respective filter member.

8. The system for deodorizing air of claim 1, each of the passive filter member and the second filter element comprising a container having at least two sides comprised of an air pervious material with the sodium bicarbonate positioned between the at least two sides of air pervious material.

9. The system for deodorizing air of claim 8, each container comprising a bag made of air pervious material with the sodium bicarbonate positioned therein.

10. The system for deodorizing air of claim 1, the first filter medium and the second filter medium each further comprising activated carbon.

11. The system for deodorizing air of claim 1, the second filter element being held in place on the air moving member by gravitational force and by surface topology of interfacing parts of the second filter element and the air moving member.

12. The system for deodorizing air of claim 11, the interfacing parts of the second filter element and the air moving member having complementary hemispherical shapes.

13. The system for deodorizing air of claim 11, the second filter element being removable from the air moving member by lifting the second filter element upwardly.

14. The system for deodorizing air of claim 11, at least one of the second filter element and the passive filter member comprising a scent substance adapted to be emitted into the atmosphere.

* * * * *

UNITED STATES PATENT AND TRADEMARK OFFICE
CERTIFICATE OF CORRECTION

| | | |
|---|---|---|
| PATENT NO. | : 7,431,901 B2 | Page 1 of 6 |
| APPLICATION NO. | : 09/775999 | |
| DATED | : October 7, 2008 | |
| INVENTOR(S) | : Paul Stiros et al. | |

It is certified that error appears in the above-identified patent and that said Letters Patent is hereby corrected as shown below:

- Title Page Illustrating a Figure should be deleted, replace with new Title Page, (Attached)

- Delete Drawing Sheets 1-4, and insert Drawing Sheets 1-4 (Attached)

- Col. 8, Line 34, delete "comer" and insert --corner--

Signed and Sealed this

Second Day of March, 2010

David J. Kappos
*Director of the United States Patent and Trademark Office*

(12) United States Patent
Stiros et al.

(10) Patent No.: US 7,431,901 B2
(45) Date of Patent: *Oct. 7, 2008

(54) APPARATUS AND METHOD FOR DEODORIZING CONFINED AIR SPACES WHICH UTILIZE BAKING SODA

(75) Inventors: Paul Stiros, Cincinnati, OH (US); Jeffrey Donald Painter, Loveland, OH (US); Frank Andraj Kvietok, Cincinnati, OH (US); Charles Michael Hardy, Norwood, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 167 days.

This patent is subject to a terminal disclaimer.

(21) Appl. No.: 09/775,999

(22) Filed: Feb. 2, 2001

(65) Prior Publication Data
US 2002/0106303 A1 Aug. 8, 2002

(51) Int. Cl.
*A61L 9/00* (2006.01)
*A62B 7/08* (2006.01)
*B01J 3/00* (2006.01)
*B01D 47/00* (2006.01)
*B01D 24/00* (2006.01)

(52) U.S. Cl. .................. 422/306; 422/1; 422/5; 422/120; 422/122; 422/123; 422/124; 422/242; 422/300; 96/153; 96/154; 96/222; 96/226; 55/528; 55/479; 261/88

(58) Field of Classification Search .......... 422/1, 422/5, 120, 122–124, 242, 300, 306; 96/153–154, 96/223, 226, 222; 55/246, 528, DIG. 5, DIG. 302, 55/479, 24, DIG. 30, 240; 261/DIG. 88
See application file for complete search history.

(56) References Cited
U.S. PATENT DOCUMENTS
5,918 A * 11/1848 Kirkwood .............. 188/168
(Continued)

FOREIGN PATENT DOCUMENTS
FR 2.189.076 1/1974
(Continued)

*Primary Examiner*—Jill Warden
*Assistant Examiner*—Monzer R Chorbaji
(74) *Attorney, Agent, or Firm*—Brent M. Peebles; Kim W. Zerby (57) ABSTRACT

Apparatus and methods for removing malodor from the air, particularly from confined spaces are disclosed. Such devices and methods are useful for example for storing and preserving food in closed compartments such as refrigerators. The apparatus and methods utilize baking soda as the odor removing substance, either alone, or in combination with another odor removing substance, which may include activated carbon. In one embodiment, the apparatus has a detachable cartridge member which contains baking soda. In one version of this embodiment, the detachable cartridge member is used with an air moving member that draws air through the detachable cartridge member. In one embodiment, the method involves using a detachable cartridge member with an air moving member in one confined space, and using another cartridge member without the air moving member in another compartment of the confined space. In another embodiment, may also be used for emitting a scent, or other substance (including, but not limited to insecticides, air fresheners, deodorants, aromacology, aromatherapy, or any other odor that acts to condition, modify, or otherwise charge the atmosphere or to modify the environment) into the air.

14 Claims, 4 Drawing Sheets